US007832410B2

(12) United States Patent
Hon

(10) Patent No.: US 7,832,410 B2
(45) Date of Patent: Nov. 16, 2010

(54) ELECTRONIC ATOMIZATION CIGARETTE

(75) Inventor: Lik Hon, Hong Kong (CN)

(73) Assignee: Best Partners Worldwide Limited, Tortola (VG)

( * ) Notice: Subject to any disclaimer, the term of this patent is extended or adjusted under 35 U.S.C. 154(b) by 600 days.

(21) Appl. No.: 10/587,707

(22) PCT Filed: Mar. 18, 2005

(86) PCT No.: PCT/CN2005/000337

§ 371 (c)(1),
(2), (4) Date: Mar. 9, 2007

(87) PCT Pub. No.: WO2005/099494

PCT Pub. Date: Oct. 27, 2005

(65) Prior Publication Data

US 2007/0267031 A1 Nov. 22, 2007

(30) Foreign Application Priority Data

Apr. 14, 2004 (CN) .................... 2004 2 0031182 U

(51) Int. Cl.
*A24F 47/00* (2006.01)
*A61M 15/06* (2006.01)
(52) U.S. Cl. ............. 131/273; 128/200.14; 128/202.21; 131/347; 131/359; 131/360
(58) Field of Classification Search .................. 131/273, 131/347, 359, 360; 128/200.14, 202.21
See application file for complete search history.

(56) References Cited

U.S. PATENT DOCUMENTS 4,228,925 A 10/1980 Mendelovich (Continued)

FOREIGN PATENT DOCUMENTS

CA 2562581 A1 10/2005

(Continued)

OTHER PUBLICATIONS

Australian Patent Office Examination Report for SG 200505930-8 dated May 4, 2006 (3 pages).

(Continued)

*Primary Examiner*—Eric Hug
*Assistant Examiner*—Anthony J Calandra
(74) *Attorney, Agent, or Firm*—Perkins Coie LLP

(57) ABSTRACT

The invention relates to an electronic atomization cigarette which only contains nicotine without harmful tar. The electronic atomization cigarette includes a shell and a mouthpiece. The external wall of the shell has an air inlet. An electronic circuit board, a normal pressure cavity, a sensor, a vapor-liquid separator, an atomizer, a liquid-supplying bottle are sequentially provided within the shell, wherein the electronic circuit board comprises an electronic switching circuit and a high frequency generator. A stream passage of the sensor is provided on one side of the sensor, and a negative pressure cavity is provided in the sensor. The atomizer and the liquid-supplying bottle is in contact with each other. An atomization cavity is arranged in the atomizer. A retaining ring for locking the liquid-supplying bottle is provided between one side of the liquid-supplying bottle and the shell, and an aerosol passage is provided on the other side of the liquid-supplying bottle. The air inlet, normal pressure cavity, vapor-liquid separator, atomizer, aerosol passage, gas vent and mouthpiece are sequentially interconnected.

27 Claims, 5 Drawing Sheets

U.S. PATENT DOCUMENTS

| | | | |
|---|---|---|---|
| 4,641,053 A * | 2/1987 | Takeda | 310/317 |
| 4,848,374 A * | 7/1989 | Chard et al. | 131/330 |
| 4,945,929 A | 8/1990 | Egilmex | |
| 4,945,931 A | 8/1990 | Gori | |
| 5,042,470 A * | 8/1991 | Kanesaka | 128/202.22 |
| 5,080,114 A | 1/1992 | Rudolph et al. | |
| 5,095,921 A | 3/1992 | Losee et al. | |
| 5,190,060 A | 3/1993 | Gerding et al. | |
| 5,322,075 A | 6/1994 | Deevi et al. | |
| 5,666,978 A | 9/1997 | Counts et al. | |
| 5,743,251 A | 4/1998 | Howell et al. | |
| 5,894,841 A | 4/1999 | Voges | |
| 6,040,560 A | 3/2000 | Fleischhauer et al. | |
| 6,178,969 B1 | 1/2001 | St. Charles | |
| 6,196,218 B1 | 3/2001 | Voges | |
| 6,357,671 B1 * | 3/2002 | Cewers | 239/102.2 |
| 6,443,146 B1 | 9/2002 | Voges | |
| 6,532,965 B1 | 3/2003 | Abhulimen et al. | |
| 6,854,461 B2 | 2/2005 | Nichols et al. | |
| 2005/0016550 A1 * | 1/2005 | Katase | 131/194 |

FOREIGN PATENT DOCUMENTS

| | | |
|---|---|---|
| CN | 2047485 | 11/1989 |
| CN | 2047485 U | 11/1989 |
| CN | 1135860 | 11/1996 |
| CN | 2293957 Y | 10/1998 |
| CN | 1252961 | 5/2000 |
| CN | 1196660 A | 3/2010 |
| DE | 100 51 792 | 5/2002 |
| EP | 0 295 122 A2 | 12/1988 |
| EP | 0342538 | 11/1989 |
| EP | 0545186 | 6/1993 |
| EP | 0 824 927 A | 2/1998 |
| EP | 0 845 220 A1 | 6/1998 |
| EP | 0 893 071 A1 | 1/1999 |
| EP | 0 970 627 A1 | 1/2000 |
| GB | 1528391 A | 10/1978 |
| JP | 64-000498 U | 1/1989 |
| JP | 06-114105 A | 4/1994 |
| JP | 07-506999 A | 8/1995 |
| JP | 09-075058 A | 3/1997 |
| UA | 47514 C2 | 12/1997 |
| WO | 97/48293 | 12/1997 |
| WO | WO 00/49901 | 8/2000 |
| WO | WO 00/50111 | 8/2000 |
| WO | 03/034847 | 1/2003 |
| WO | 03/022364 A1 | 3/2003 |
| WO | WO 03/055486 | 7/2003 |
| WO | WO 03/101454 | 12/2003 |
| WO | 2004/080216 | 9/2004 |
| WO | WO 2004/095955 | 11/2004 |
| WO | WO 2005/099494 | 10/2005 |

OTHER PUBLICATIONS

Supplementary Partial European Search Report for EP04718242 dated May 22, 2007 (4 pages).
Supplementary European Search Report for EP04718242 dated Jul. 27, 2007 (7 pages).
Supplementary Partial European Search Report for EP05729107 dated May 22, 2007 (4 pages).
Supplementary European Search Report for EP05729107 dated Jul. 31, 2007 (6 pages).
International Search Report for International Application No. PCT/CN2005/000337 dated Jul. 14, 2005 (3 pages).
International Search Report for International Application No. PCT/CN2004/000182 dated Jun. 10, 2004 (2 pages).
Malaysia Intellectual Property Office; Examiner's Report for Malaysian Application No. PI 20041407, dated Sep. 28, 2007.
Australian Patent Office; Singapore Examination Report for Singapore Patent Application No. 0604498-6, mailed May 13, 2008.
Australian Patent Office, Exam Report for AU2004234199 dated Aug. 14, 2009.
Singapore Patent Office, Search and Examination Report for SG200604498-6 dated Apr. 16, 2008.
European Patent Office, Supplementary European Search Report for EP05729107.2 dated Oct. 10, 2007.
Japanese Patent Office, Office Action for JP2006-504199 dated Oct. 30, 2009 (English translation included).
Korean Patent Office, Notice of Preliminary Rejection for KR10-2005-7009767 dated Jul. 27, 2009 (English translation included).
Macau Patent Office, Official Communication for MOI/121 dated Apr. 17, 2009.
Taiwan Intellectual Property Office, Official Letter for TW093111573 dated April 24, 2009 (English translation included).
Ukrainian Patent Office, Examination Report for UK2005-11258 dated Feb. 4, 2009.

* cited by examiner

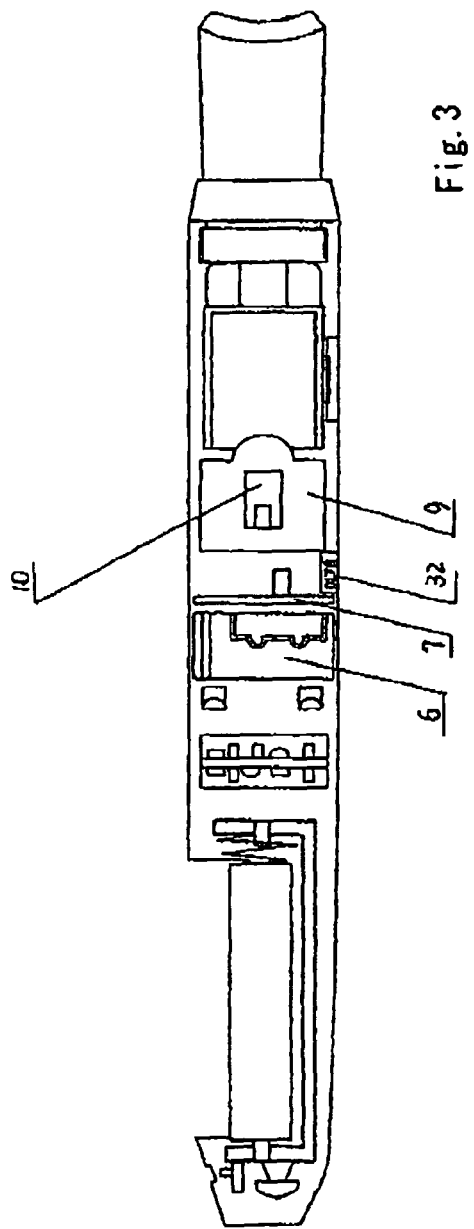
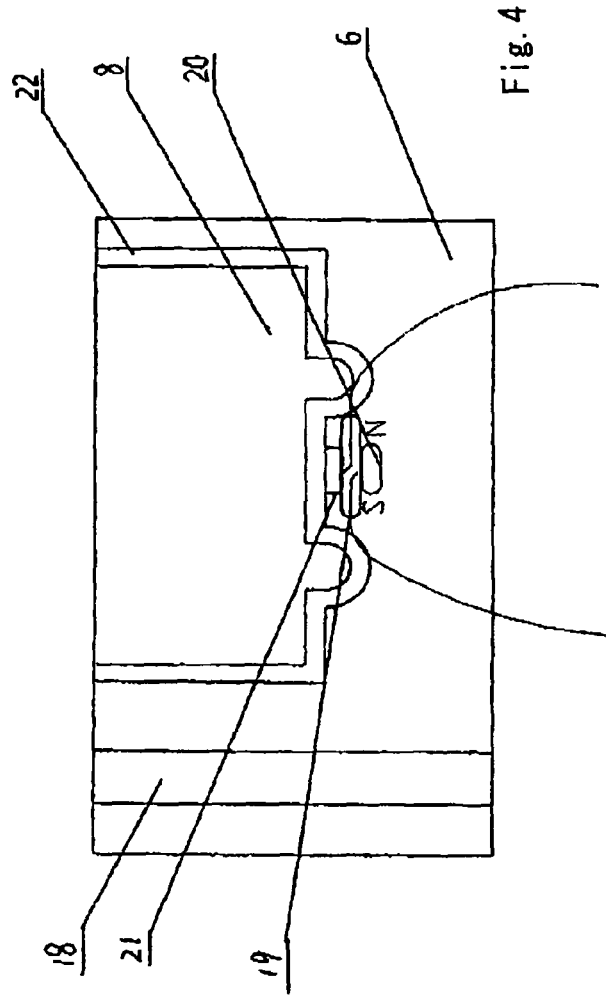

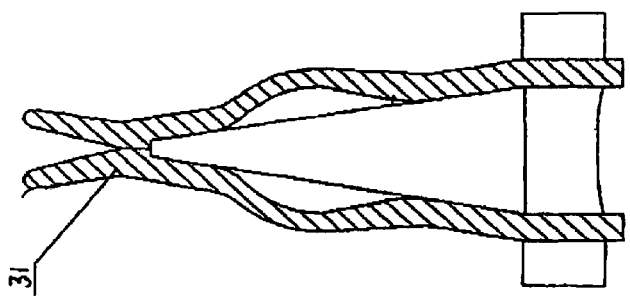
Fig. 10
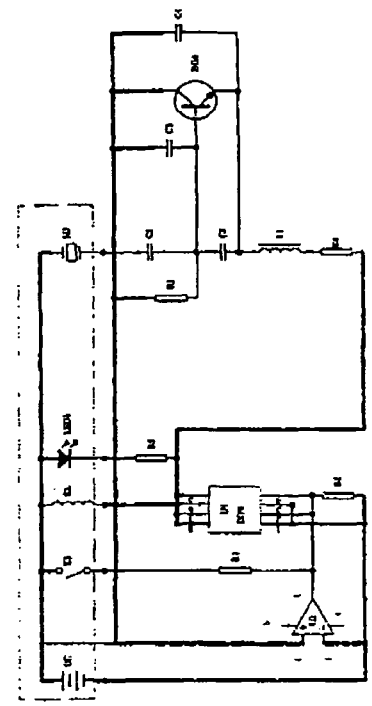
Fig. 12
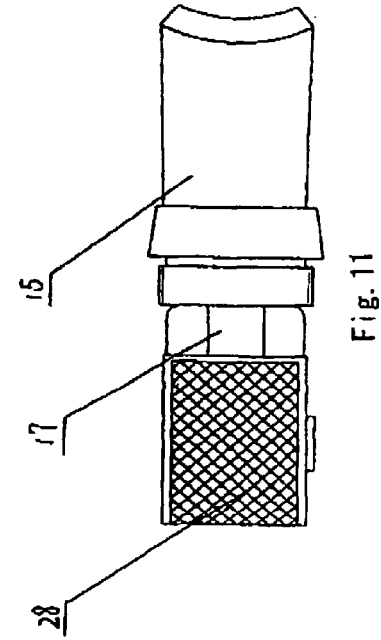
Fig. 9
Fig. 11

ELECTRONIC ATOMIZATION CIGARETTE

TECHNICAL FIELD

The present invention relates to an electronic cigarette, in particular to an electronic atomization cigarette that contains only nicotine without tar.

BACKGROUND ART

Despite it is commonly known that "smoking is harmful to your health", the number of smokers worldwide is up to 1 billion, and the number is increasing every year. On Mar. 1, 2003, the World Health Organization (WHO) concluded a global Framework Convention on Tobacco Control. According to the statistical data from WHO, about 4.9 million people die of is diseases caused by smoking each year. Although smoking may cause serious respiratory diseases and cancer, it remains extremely difficult for smokers to quit smoking completely.

The active ingredient in a cigarette is nicotine. During smoking, nicotine, along with a lot of tar aerosol droplets produced in the cigarette burning, enters smoker's alveolus and is rapidly absorbed. After being absorbed into the blood of a smoker, nicotine then produces its effect on the receptors of the smoker's central nervous system, which makes him/her relax and enjoy an inebriety similar to that produced by an exhilarant.

Nicotine is a kind of alkaloid with low molecular weight and its half-life in blood is quite short. The major harmful subsatance in tobacco is tar, tar in tobacco is composed of thousands of ingredients, tens of which are carcinogenic substances. At present it has been proven that passive smoking can be more harmful to non-smokers.

Some cigarette substitutes flat contain only nicotine without tar have been proposed, many of them, such as "nicotine patch", "nicotine mouthwash", "spray agent packaged in high pressure gas tank with propellant", "nicotine chewing gum", "nicotine drink" etc., are made of pure nicotine. Although these cigarette substitutes are free from tar, their major disadvantage is that an effective peak concentration can not be reached in the blood of a smoker due to slow absorption of nicotine and thus it can not make a smoker get real fin, in addition, these cigarette substitutes can not satisfy habitual smoking actions of a smoker, for example, inhaling action or sucking action, and thus are not likely to be widely accepted as effective substitutes for quitting smoking or cigarette substitutes.

THE SUMMARY OF THE INVENTION

To overcome the above-referenced drawbacks, an objective of the present invention is to provide an electronic atomization cigarette that may function as a substitute for smoking cessation products or as a cigarette substitute.

The objective of the present invention is achieved by the following technical solution.

The present invention includes a shell; a mouthpiece; an air inlet provided in the external wall of the shell; an electronic circuit board, a normal pressure cavity, a sensor, a vapor-liquid separator, an atomizer, a liquid-supplying bottle arranged sequentially within the shell; a stream passage provided on one side of the sensor; a negative pressure cavity provided in the sensor; an atomization cavity arranged in the atomizer; a retaining ring for locking the liquid-supplying bottle provided between one side of the liquid-supplying bottle and the shell; and an aerosol passage provided on the other side of the liquid-supplying bottle, wherein the electronic circuit board comprises an electronic switching circuit and a high frequency generator; the liquid-supplying bottle is in contact with the atomizer; and the air inlet, normal pressure cavity, vapor-liquid separator, atomizer, aerosol passage, gas vent and mouthpiece are sequentially interconnected. A LED and a cell are provided at the front end within the shell, collectively constituting an integrity like a cigarette holder, cigar or a pipe.

Furthermore, a display screen is additionally provided on the inner wall of the shell; a microswitch for manually cleaning is connected to the sensor in parallel connection within the shell; a ripple film is provided between the sensor and the negative pressure cavity inside the sensor; a first magnetic steel, a second magnetic steel and a Reed switch connected between them provided within the sensor, wherein the second magnetic steel is attached to the ripple film: a silicon gel check valve is provided within the sensor, a third magnetic steel is provided in the silicon gel check valve, and a Reed switch is provided outside the valve, on the side close to the magnetic steel; a through hole is arranged on the vapor-liquid separator, a silicon gel check valve covers the through hole on the vapor-liquid separator; a overflow hole is provided on the atomization cavity wall of the atomization cavity, a heating element is provided within the atomization cavity, a long stream ejection hole is provided on one side of the heating element, the porous body is arranged outside around the atomization cavity wall, the first piezoelectric element is provided on one side of the atomizer, and a bulge is provided on the other side; the second piezoelectric element is additionally provided in the atomizer; the porous body in the atomizer can be made of foam nickel, stainless steel fiber felt, high molecule polymer foam and foam ceramic; the heating element can be made of platinum wire, nickel chromium alloy or iron chromium aluminum alloy wire with rare earth element, or may be made into a sheet form with conductive ceramics or PTC ceramics; the atomization cavity wall can be made of aluminum oxide or ceramic; the vapor-liquid separator can be made of plastic or silicon rubber; the solution storage porous body is included in the liquid-supplying bottle, and can be filled with polypropylene fiber, terylene fiber or nylon fiber, or be filled with plastics that are shaped by foaming; alternatively, it may be modeled into a column with laminated layers by polyvinyl chloride, polypropylene, polycarbonate; the Reed switch, the first magnetic steel, the second magnetic steel, the ripple film can be replaced by a semiconductor strain gauge with sealed film, which is mounted in the place of the sensor ripple film.

The present invention also discloses an electronic atomization cigarette with another structure, wherein the atomizer is postposed within the shell, the liquid-supplying bottle is arranged between the vapor-liquid separator and the atomizer, and a spring piece for pressing the liquid-supplying bottle on the atomizer is arranged at one end of the liquid-supplying bottle.

The advantages of the present invention include smoking without tar, significantly reducing the cancerogenic risk. Furthermore users still feel as if they are smoking and experiencing the same excitement, and the cigarette is no need to be lit and is no fire risk.

With slight modification of the solution storage container, the device and connecting structures of the present invention can be filled with conventional drug for pulmonary administration apparatus.

DESCRIPTION OF THE DRAWINGS

FIG. 3 is a schematic diagram of a overall structure with a display screen according to the present invention;

FIG. 4 is a structural diagram of a sensor according to the present invention;

FIG. 9 is a structural diagram of a vapor-liquid separator according to the present invention;

FIG. 10 is a structural diagram of another vapor-liquid separator according to the present invention;

FIG. 11 is a structural diagram of the connection of a liquid-supplying bottle and a mouthpiece according to the present invention;

FIG. 12 is a functional diagram of a circuit according to the present invention.

DETAILED DESCRIPTION OF THE INVENTION

The present invention is further described below with reference to the accompanying drawings.

Embodiment 1

Figure 1:
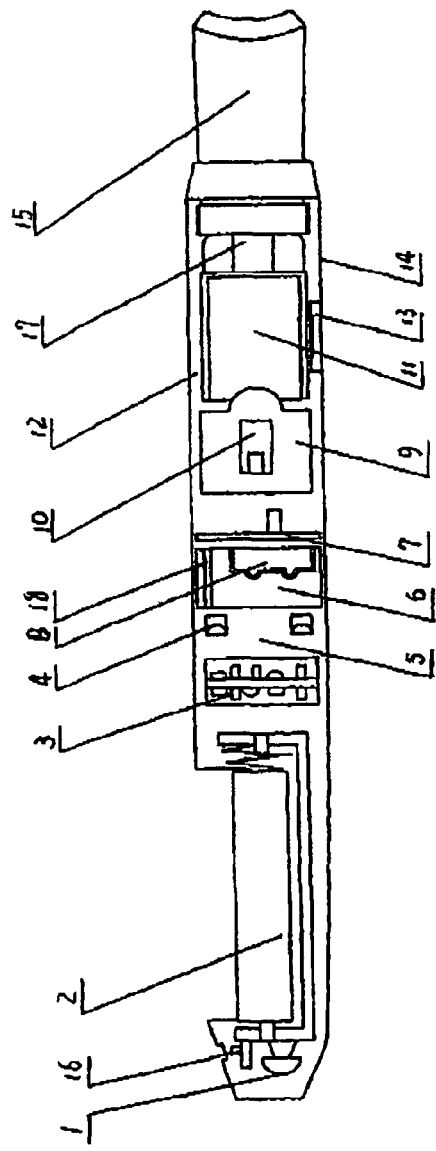
FIG. 1 is a schematic diagram of an overall structure according to the present invention.
Figure 6:
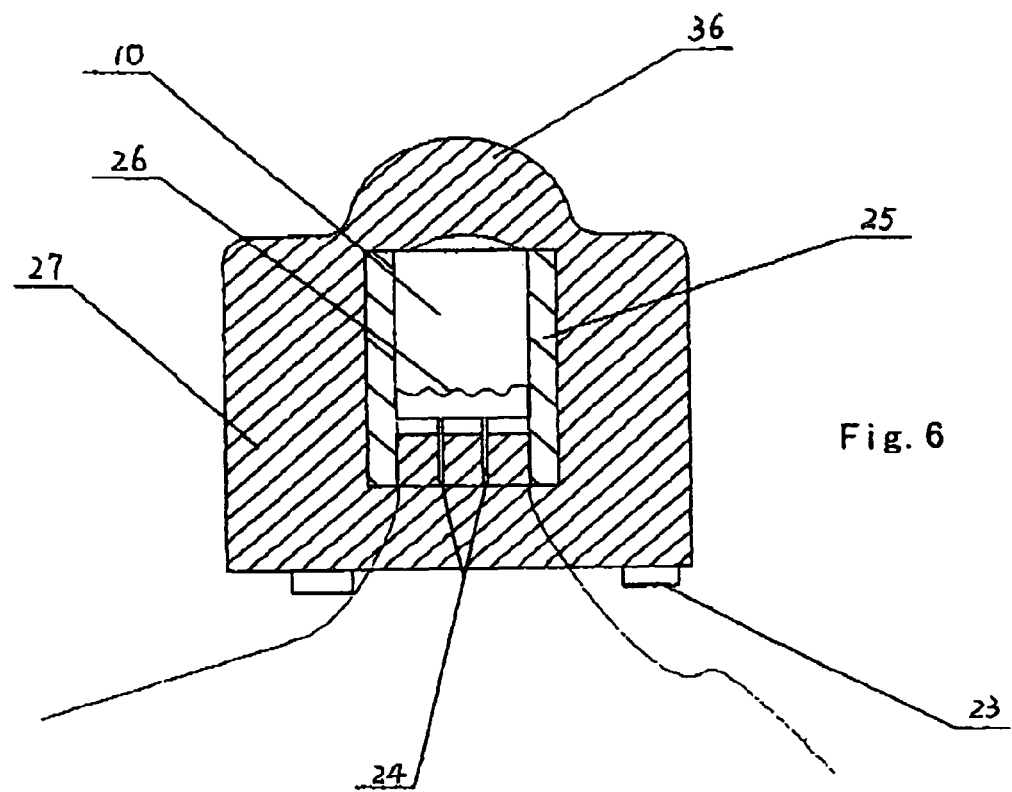
FIG. 6 is a structural diagram of an atomizer according to the present invention.
Figure 7:
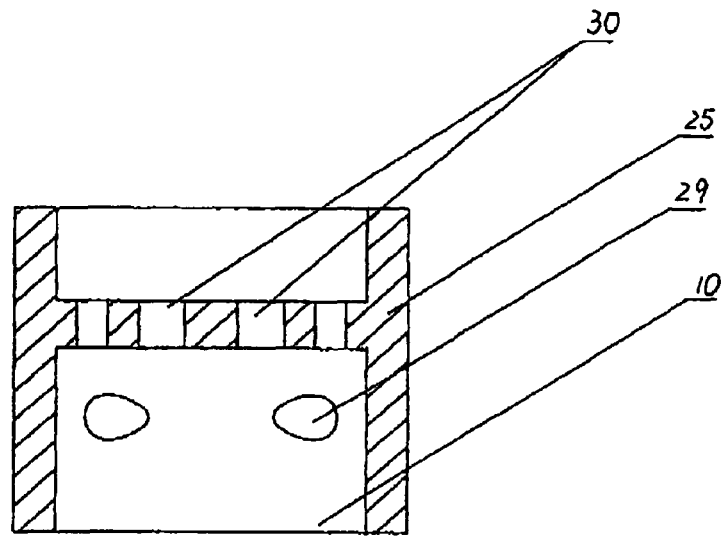
FIG. 7 is a structural diagram of the ceramic member in an atomizer according to the present invention.

As shown in FIG. 1, the present invention can form an integrity like a cigarette holder, a cigar or a pipe. An air inlet 4 is provided on the external wall of the shell 14. A LED 1, a cell 2, an electronic circuit board 3, a normal pressure cavity 5, a sensor 6, a vapor-liquid separator 7, an atomizer 9, a liquid-supplying bottle 11 and a mouthpiece 15 are sequentially provided within the shell 14. The electronic circuit board 3 comprises an electronic switching circuit and a high frequency generator. As shown in FIG. 4, a negative pressure cavity 8 is provided in the sensor 6 and is separated from the sensor 6 by a ripple film 22. A first magnetic steel 20, a second magnetic steel 21 and a Reed switch 19 arranged between them is also provided within the sensor 6, and the second magnetic steel 21 is attached to the ripple film 22. The atomizer 9 is in contact with the liquid-supplying bottle 11 via the bulge 36, and the atomization cavity 10 is provided in the atomizer 9. As shown in FIGS. 6 and 7, the overflow hole 29 is provided on the atomization cavity wall 25 of the atomization cavity 10. A heating element 26, which can be made of platinum wire, nickel chromium alloy or iron chromium aluminum alloy wire with rare earth element, is provided within the cavity, and can also be made into a sheet form with conductive ceramics or PTC ceramics. An ejection hole is provided on the side opposite to the heating element 26 and the ejection hole can be determined to select either the long stream ejection hole 24 or the short stream ejection hole 30, depending on the material used for the atomization cavity wall 25. The long stream ejection hole 24 can employ slot structure of 0.1 mm-1.3 mm or circular hole structure of Φ0.2 mm-1.3 mm with a single and multiple holes. The short stream ejection hole 30 has the diameter of about 0.3 mm-1.3 mm. The atomization cavity wall 25 is surrounded with the porous body 27, which can be made of foam nickel, stainless steel fiber felt, high molecule polymer foam and foam ceramic. A first piezoelectric element 23 is also provided on the atomizer 9. The atomization cavity wall 25 can be made of aluminum oxide or ceramic. As shown in FIG. 9, a through hole is provided on the vapor-liquid separator 7, and can be made of plastic or silicon rubber. As shown in FIG. 11, a retaining ring 13 for locking the liquid-supplying bottle 11 is provided between one side of the liquid-supplying bottle 11 and the shell 14, an aerosol passage 12 is provided on the other side of the liquid-supplying bottle. The solution storage porous body 28 is provided in the liquid-supplying bottle, and can be filled with polypropylene fiber, terylene fiber or nylon fiber, or be filled with plastic that are shaped by foaming, such as polyamine resin foam column or polypropylene foam column; alternatively, it may be made of a column formed by molding polyvinyl chloride, polypropylene, polycarbonate into a stack of laminated layers. The air inlet 4, normal pressure cavity 5, vapor-liquid separator 7, atomizer 9, aerosol passage 12, gas vent 17, mouthpiece 15 are sequentially interconnected.

As shown in the functional diagram of the circuit in FIG. 12, K1 refers to the Reed switch 19, RL refers to the heating element 26, LED1 refers to the Light Emitting Diode 1, U2 refers to the low voltage detecting element used for the over-discharging protection of the lithium cell, M1 refers to the first piezoelectric element 23, and C1, C2, R3, L1, C3, BG, M1 collectively constitute a Colpitts oscillator. The operating principle of the circuit is as follows: when K1 is closed, U1, i.e., the field effect power transistor, is turned on, RL starts, and the Colpitts oscillator starts oscillating, M1 will provide the high frequency mechanical oscillatory wave to the atomizer 9 to achieve the result of atomization.

When a smoker smokes, the mouthpiece 15 is under negative pressure, the air pressure difference or high speed stream between the normal pressure cavity 5 and the negative pressure cavity 8 will cause the sensor 6 to output an actuating signal, the electronic circuit board 3 connected therewith goes into operation. Now the ripple film 22 in the sensor 6 is deformed to take the second magnetic steel 21 away from the Reed switch 19, and the Reed switch 19 is then closed (i.e., K1 is closed) under the effect of the excessive magnetic line of force from the first magnetic steel 20, starting the field effect power. The high frequency oscillator may uses the Colpitts oscillator with the frequency of automatic fine-adjusting element in the circuit resonates with the first piezoelectric element 23 in the form of a ring to supply power to liquid molecule, and the LED 1 can be lit under the supply of the rechargeable battery 2. The air enters the normal pressure cavity 5 through the air inlet 4, passes through the air passage 18 of the sensor and then the through hole in the vapor-liquid separator 7, and flows into the atomization cavity 10 in the atomizer 9. The high speed stream passing through the ejection hole drives the nicotine solution in the porous body 27 to eject into the atomization cavity 10 in the form of droplet, where the nicotine solution is subjected to the ultrasonic atomization by the first piezoelectric element 23 and is further atomized by the heating element 26. After the atomization the droplets with large diameter stick to the wall under the action of eddy flow and are reabsorbed by the porous body 27 via the overflow hole 29, whereas the droplets with small diameter float in stream and forms aerosols, which are sucked out via the aerosol passage 12, gas vent 17 and mouthpiece 15. The solution storage porous body 28 in the liquid-supplying bottle 11 will be in contact with the bulge 36 on the atomizer 9, thereby achieving the capillary infiltration liquid-supplying.

The mouthpiece 15 is threaded. When the nicotine solution in the liquid-supplying bottle 11 is used up, users can screw the mouthpiece 15 out to take the liquid-supplying bottle 11 out, refill the liquid-supplying bottle 11 with the nicotine solution, put the liquid-supplying bottle 11 into the shell 14 again, and then screw the mouthpiece 15.

The Reed switch 19, the first magnetic steel 20, the second magnetic steel 21, the ripple film 22 can be replaced by a semiconductor strain gauge with sealed film, which is mounted in the place of the sensor ripple film.

Figure 8:
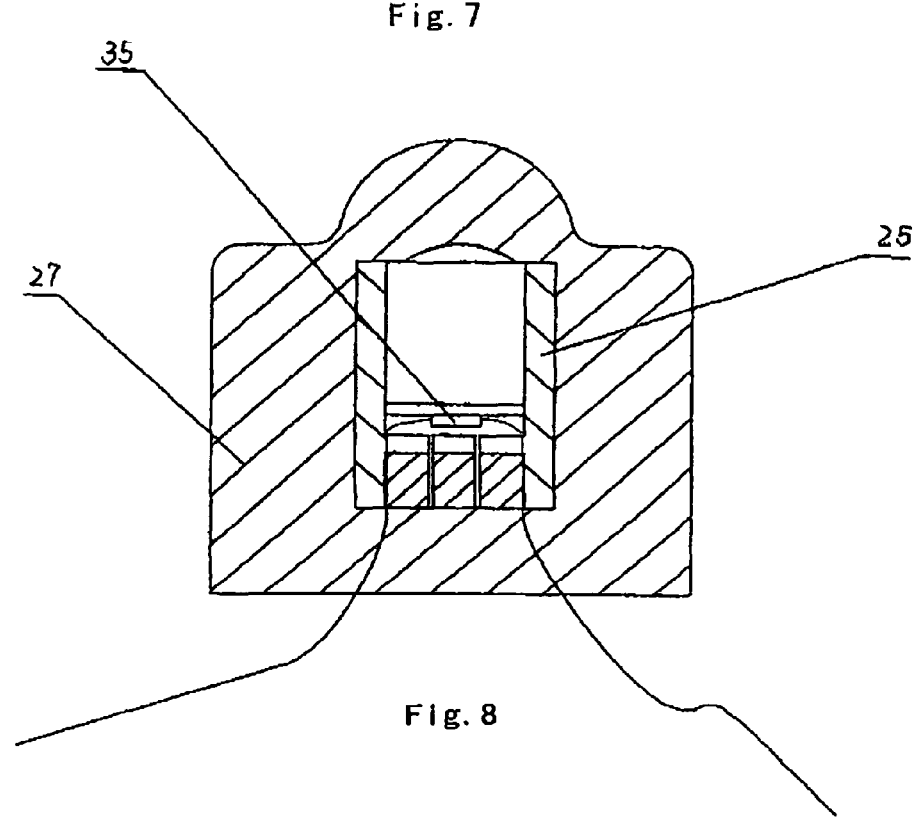
FIG. 8 is a structural diagram of another atomizer according to the present invention.

To simplify the design, the first piezoelectric element 23 on the atomizer 9 can be omitted, and the atomization of the nicotine solution will be made only by the heating element 26. The size of such an atomizer can be made smaller, and the structure of the connection of the whole electronic atomization cigarette is the same as the embodiment 1. In addition, as shown FIG. 8, the first piezoelectric element 23 and the heating element 26 in the atomizer 9 can be omitted, an additional second piezoelectric element 35 in the form of platen with a single layer or multiple laminated layers can be arranged in the atomization cavity, and the stream passing through the ejection hole vibrates the focus at the center of the second piezoelectric element 35 to achieve the effect of strong ultrasonic atomization.

As shown in FIG. 10, a silicon gel check valve 31 may cover the outside of the through hole on the vapor-liquid separator 7. During smoking, a stream reaches the through hole, as the air pressure in the through hole increases, the silicon gel check valve 31 is opened and the stream passes; otherwise, the silicon gel check valve 31 is closed.

Figure 5:
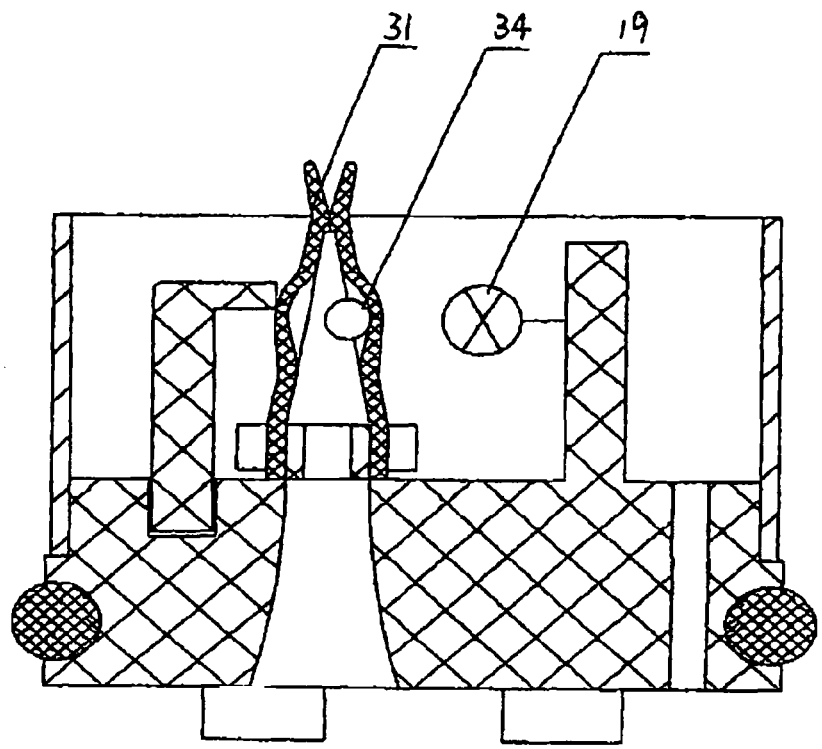
FIG. 5 is a structural diagram of a sensor with a silicon gel check valve according to the present invention.

As shown in FIG. 5, the sensor 6 may also be designed into a structure with the silicon gel check valve 31. During smoking, the stream comes into the silicon gel check valve 31, the air pressure increases and the air expands, the third magnetic steel 34 in the valve approaches the Reed switch 19 gradually until the Reed switch is closed and the circuit is turned on, and the air outlet of the silicon gel check valve 31 is opened with the increment of the air pressure difference. The Reed switch 19 can also be made of Hall device or magneto diode or magneto triode instead.

Embodiment 2

Figure 2:
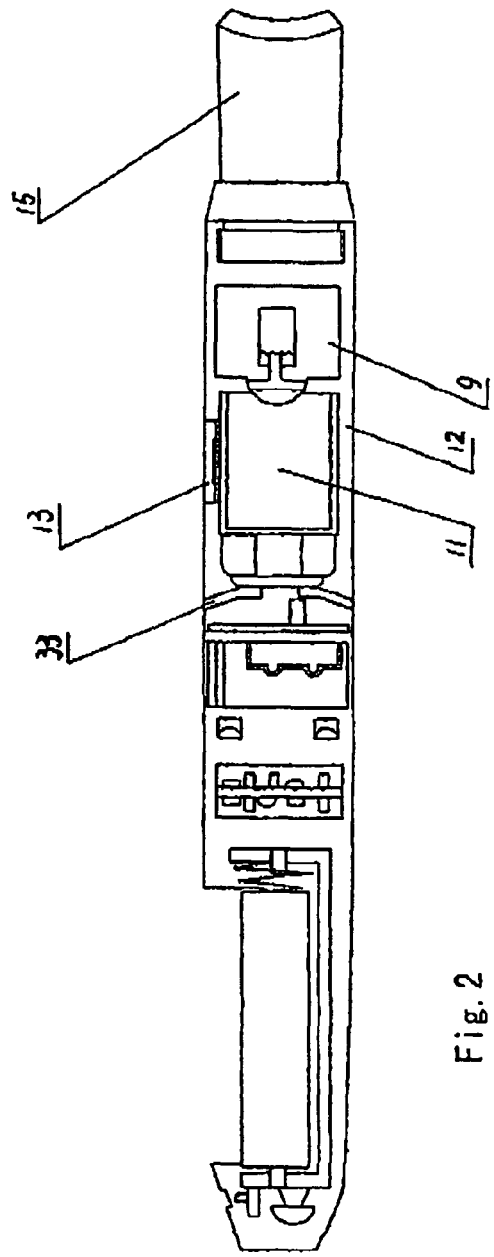
FIG. 2 is a schematic diagram of another overall structure according to the present invention.

As shown in FIG. 2, to improve the liquid-supplying state, the atomizer 9 is postposed within the shell 14, and the liquid-supplying bottle 11 is arranged between the vapor-liquid separator 7 and the atomizer 9. A spring piece 33 for pressing the liquid-supplying bottle 11 on the atomizer 9 is provided on one end of the liquid-supplying bottle 11. Other components and their functions are the same as those in the embodiment 1.

On the inner wall of the shell 14 of the electronic atomization cigarette described in the embodiment 1 and 2, a digital display screen 32 for showing the smoking times per day and the cell capacity can be also provided. The sensor 6 uses a linear signal output, which is proportional to the suction force (i.e., the stronger one sucks, the longer the time of operation is), the atomizer 9 operates in the linear mode, thereby simulating a humanized cigarette that looks like a normal cigarette.

Within the shell 14, the microswitch 16 is connected to the sensor 6 in parallel and used for manually cleaning. When users do not smoke, they press the microswitch 16 to start the sensor 6 connected therewith in parallel, or clean the residue or other impurity substance within the shell 14.

The nicotine solution for atomization contains 0.4-3.5% nicotine, 0.05-2% cigarette essence, 0.1-3.1% organic acid, 0.1-0.5% anti-oxidation agent, and the rest is 1,2-propylene glycol.

What is claimed is:

1. An electronic atomization cigarette, comprising:
   a shell;
   a mouthpiece;
   an air inlet provided on the external wall of the shell;
   a cell, an electronic circuit board, a normal pressure cavity, a sensor, a vapor-liquid separator, an atomizer, a liquid-supplying bottle arranged sequentially within the shell;
   a stream passage provided on one side of the sensor;
   a gas vent;
   a negative pressure cavity provided in the sensor;
   an atomization cavity arranged in the atomizer;
   an aerosol passage provided on one side of the liquid-supplying bottle;
   wherein the liquid-supplying bottle is in contact with the atomizer;
   a ripple film provided between the sensor and the negative pressure cavity within the sensor;
   a first magnetic steel, a second magnetic steel and a magneto device connected between said first and second magnetic steel provided within the sensor, wherein the second magnetic steel is attached to the ripple film; and
   the air inlet, normal pressure cavity, vapor-liquid separator, atomizer, aerosol passage, the gas vent and mouthpiece are sequentially interconnected.

2. The electronic atomization cigarette according to claim 1, wherein the magneto device is a Reed switch.

3. The electronic atomization cigarette according to claim 1, wherein the magneto device is a Hall device.

4. The electronic atomization cigarette according to claim 1, wherein the magneto device is a magneto diode.

5. The electronic atomization cigarette according to claim 1, wherein the magneto device is a magnetic triode.

6. The electronic atomization cigarette according to claim 1, further comprising:
   a silicon gel check valve provided within the sensor;
   a third magnetic steel provided in the silicon gel check valve; and
   a Reed switch provided outside the silicon gel check valve, on a side close to the magnetic steel.

7. The electronic atomization cigarette according to claim 1, further comprising:
   a heating element provided within the atomization cavity;
   a stream ejection hole provided on one side of the heating element; and
   a porous body arranged outside around a wall of the atomization cavity.

8. The electronic atomization cigarette according to claim 1, further comprising:
   a first piezoelectric element provided on one side of the atomizer; and
   a bulge provided on the other side of the atomizer.

9. The electronic atomization cigarette according to claim 7, wherein the stream ejection hole is a long stream ejection hole with 0.1 mm-1.3 mm of slot structure.

10. The electronic atomization cigarette according to claim 7, wherein the stream ejection hole is a long stream ejection hole with φ0.2 mm-1.3 mm of circular hole structure having a single and multiple holes.

11. The electronic atomization cigarette according to claim 7, wherein the stream ejection hole is a short stream ejection hole with a diameter of 0.3 mm-1.3 mm.

12. The electronic atomization cigarette according to claim 1, further comprising:
    a piezoelectric element provided in the atomizer, wherein a stream passing through an ejection hole is atomized at a central vibration focus of the piezoelectric element to achieve an effect of strong ultrasonic atomization.

13. The electronic atomization cigarette according to claim 12, wherein the piezoelectric element comprises a platen with a single layer.

14. The electronic atomization cigarette according to claim 12, wherein the piezoelectric element comprises a platen with laminated layers.

15. The electronic atomization cigarette according to claim 1, wherein the atomizer is surrounded by a porous body which can be made of foam nickel, stainless steel fiber felt, high molecule polymer foam and foam ceramic.

16. The electronic atomization cigarette according to claim 7, wherein the heating element is made of platinum wire, nickel chromium alloy or iron chromium aluminum alloy wire with rare earth element.

17. The electronic atomization cigarette according to claim 7, wherein the heating element is made into a sheet comprising ceramics.

18. The electronic atomization cigarette according to claim 1, wherein the atomization cavity comprises a wall made of aluminum oxide.

19. The electronic atomization cigarette according to claim 1, wherein the atomization cavity comprises a wall made of ceramics.

20. An electronic atomization cigarette, comprising:
    a shell;
    a mouthpiece;
    an air inlet provided on the external wall of the shell;
    a cell, an electronic circuit board, a normal pressure cavity, a sensor, a vapor-liquid separator, an atomizer, a liquid-supplying bottle arranged sequentially within the shell;
    a stream passage provided on one side of the sensor;
    a gas vent;
    a negative pressure cavity provided in the sensor;
    an atomization cavity arranged in the atomizer;
    an aerosol passage provided on one side of the liquid-supplying bottle, wherein the liquid-supplying bottle is in contact with the atomizer; and
    a through hole arranged on the vapor-liquid separator
    wherein the air inlet, normal pressure cavity, vapor-liquid separator, atomizer, aerosol passage, the gas vent and mouthpiece are sequentially interconnected.

21. The electronic atomization cigarette according to claim 20, further comprising:
    a silicon gel check valve covering the outside of the through hole on the vapor-liquid separator.

22. The electronic atomization cigarette according to claim 20, wherein the vapor-liquid separator is made of plastics.

23. The electronic atomization cigarette according to claim 20, wherein the vapor-liquid separator is made of silicon rubber.

24. An electronic atomization cigarette, comprising:
    a shell;
    a mouthpiece;
    an air inlet provided on the external wall of the shell;
    a cell, an electronic circuit board, a normal pressure cavity, a sensor, a vapor-liquid separator, an atomizer, a liquid-supplying bottle arranged sequentially within the shell;
    a stream passage provided on one side of the sensor;
    a negative pressure cavity provided in the sensor;
    an atomization cavity arranged in the atomizer; and
    an aerosol passage provided on one side of the liquid-supplying bottle, wherein the liquid-supplying bottle is in contact with the atomizer;
    wherein the air inlet, normal pressure cavity, vapor-liquid separator, atomizer, aerosol passage, gas vent and mouthpiece are sequentially interconnected and wherein a solution storage porous body is provided in the liquid-supplying bottle.

25. The electronic atomization cigarette according to claim 24, wherein the solution storage porous body is filled with polypropylene fiber, terylene fiber or nylon fiber.

26. The electronic atomization cigarette according to claim 24, wherein the solution storage porous body is filled with plastics that are shaped by foaming.

27. The electronic atomization cigarette according to claim 24, wherein the solution storage porous body is molded into a column with laminated layers by polyvinyl chloride, polypropylene, polycarbonate.

* * * * *